United States Patent [19]

Barabino et al.

[11] 4,247,647
[45] Jan. 27, 1981

[54] APPARATUS FOR THE QUANTITATIVE DETERMINATION OF SACCHARIDES

[75] Inventors: Raymond C. Barabino, Toledo; Melvin H. Keyes, Sylvania, both of Ohio

[73] Assignee: Technicon Instruments Corporation, Tarrytown, N.Y.

[21] Appl. No.: 886,503

[22] Filed: Mar. 14, 1978

[51] Int. Cl.$^3$ ............................................. C12M 1/34
[52] U.S. Cl. ...................................... 435/291; 435/14; 435/18; 435/25; 435/27
[58] Field of Search ................. 195/103.5 R, 103.5 C, 195/127, 115, 31 R; 204/195 B, 1 T; 435/14, 18, 22, 27, 28, 288, 176, 291

[56] References Cited

U.S. PATENT DOCUMENTS

| | | | |
|---|---|---|---|
| 3,838,011 | 9/1974 | Hagen et al. | 23/230 B |
| 3,879,263 | 4/1975 | Adams | 195/103.5 S |
| 3,902,970 | 9/1975 | Levin | 195/103.5 C |
| 3,925,018 | 12/1975 | Saunders | 435/14 |
| 4,001,085 | 1/1977 | Keyes | 435/176 |
| 4,018,651 | 4/1977 | Canto et al. | 195/103.5 C |
| 4,040,908 | 8/1977 | Clark | 195/103.5 C |
| 4,102,742 | 7/1978 | Klose et al. | 195/103.5 C |
| 4,116,773 | 9/1978 | Polito | 195/103.5 C |
| 4,169,765 | 10/1979 | Keyes | 435/291 |

OTHER PUBLICATIONS

Marshall et al., "Enzymatic Determination of Maltose by Amperometric Measurement of the Rate of Oxygen Depletion", *Analyst*, vol. 102, (1977), pp. 424–428.
Levin et al., "High-Precision Industrial Measurements with Immobilized Enzymes", presented at American Institute of Chem. Engineers, 77th National Meeting, Pittsburgh, Pa., 1974.
Trauberman, "Immobilized Enzymes Put to Work in Analysis and Control", *Food Engineering*, Leeds & Northrup, North Wales, Pa. (1975).
Gutmann, "Maltose", *Methods of Enzymatic Analysis*, vol. 3, Bergmeyer, ed., Academic Press, New York, (1974), pp. 1185–1188.
O'Neal et al., "An Automated, Saccharogenic Method for Determining Serum Amylase Activity", *Clin. Chem.*, vol. 16, No. 12, (1970), pp. 985–989.

*Primary Examiner*—Thomas G. Wiseman
*Attorney, Agent, or Firm*—S. P. Tedesco

[57] ABSTRACT

A method for the quantitative determination of sugars in a fluid sample. The sugar sample, which may contain free glucose, is passed through a scavenger stage where substantially all of the glucose is removed, so that it does not interfere with the determination. The glucose-free sample is then passed through an immobilized glucose generating stage to produce glucose in molar proportion to the total initial concentration of the sugars present. The generated glucose is passed through an immobilized hydrogen peroxide generating stage to form gluconic acid and hydrogen peroxide. The generated hydrogen peroxide is detected in suitable detection means, typically a polarographic cell. Total free glucose is determined by measuring the total sugars in the sample by bypassing the scavenger stage, determining total sugar, then determining the glucose in the sample without bypassing the scavenger and measuring free glucose as the difference.

6 Claims, 3 Drawing Figures

APPARATUS FOR THE QUANTITATIVE DETERMINATION OF SACCHARIDES

BACKGROUND OF THE INVENTION

1. Field Of The Invention

The invention relates to a method and apparatus for the determination of sugars in fluid samples. More particularly, the present invention relates to the analysis of glucose based sugars (disaccharides, oligosaccharides, and polysaccharides) in biological fluids such as blood and urine wherein free glucose may be present. Glucose is typically present in large amounts in biological fluids and may substantially interfere with the quantification of sample components which are present in smaller quantities, such as, for example, maltose, maltotriose, oligosaccharides and the like.

Presently, there is a need in clinical chemistry for an instrument and analytical technique which is capable of monitoring biological fluids for the total of the sugars present which are present in varying concentrations and when the samples to be determined are known to contain glucose and contaminating amounts. Recently, a great deal of attention has been directed towards the development of analytical methods for maltose in particular, based on the enzymatic conversions of sugars in the presence of an enzyme which is capable of reacting with the sugars to form glucose, which is a detectable end product. The present invention successfully overcomes difficulties previously encountered in sugar determination methods over wide ranges of total sugar and contaminating glucose concentrations.

2. Description Of The Prior Art

The prior art discloses that under the influence of the proper enzyme or enzymes, various sugar forms (such as disaccharides and polysaccharides) may be converted to other sugar forms. For example, U.S. Pat. No. 3,879,263 shows that in an alpha-amylase analysis, the amylase reacts with various carbohydrates to produce maltose. The maltose thus produced will react with glucoamylase, to produce glucose. These two reactions are key steps in the internal digestion of carbohydrates, especially starches.

Also, methods are known to detect various sugars in aqueous solution. U.S. Pat. No. 3,902,970 shows a method to determine glucose concentrations in solution using an amperometric detection means. The system uses the enzyme glucose oxidase to convert glucose to gluconic acid and hydrogen peroxide, with the peroxide measured in a flow-through amperometric cell to give an indication of the initial glucose concentration.

U.S. Pat. No. 4,018,651 discloses that glucose concentrations may be monitored by the rate of oxygen consumption in a glucose oxidase catalyzed reaction which consumes oxygen and produces hydrogen peroxide and gluconic acid.

Similarly, Marshall et al, "Enzymatic Determination of Maltose by Amperometric Measurement of the Rate of Oxygen Depletion", in Analyst, June 1977, Vol. 102, pp. 424–428, disclose a method for the enzymatic determination of maltose by oxygen depletion. The method converts maltose to glucose, and glucose to hydrogen peroxide and gluconic acid. The oxygen consumed in the conversion reaction is monitored by an oxygen electrode and is a measure of the glucose, and thus the maltose. The method leaves residual hydrogen peroxide which may degrade other sample components if the sample is to be used in determining multiple components. Also, the lack of the use of immobilized enzymes which can be used repeatedly, increases the cost of using the method. The contaminating glucose is removed by solution phase incubation with glucose oxidase. This also generates free hydrogen peroxide in the sample, and requires the separation of the glucose oxidase if a second substrate needs to be monitored. The method is also subject to interference by starch and sucrose.

SUMMARY OF THE INVENTION

An object of the present invention is to provide an apparatus and method for the analysis of sugars in fluids in the presence of contaminating glucose, which overcomes the disadvantages of the prior art.

A further object of the present invention is to provide an immobilized enzyme-based method for determining sugars in fluids to materially lower the time of the clinical analysis.

The method according to the present invention produces a quantitative measure of the concentration of total sugars in the presence of glucose which may be an original contaminant in the determination.

In some cases, glucose is one of the sugars which is the target of the analysis, while in some cases it is a contaminant and must be removed from the sample to remove its interference. When glucose is an original contaminant in the analysis, the method involves the passing of the sample through a scavenger stage wherein an immobilized scavenger reagent removes essentially all the glucose which contaminates the sample. The glucose-free sample flows through an immobilized glucose generating stage wherein the sugar sample is hydrolyzed to form generated glucose. The generated glucose containing sample is then passed through an immobilized hydrogen peroxide generating stage wherein the generated glucose is oxidized to gluconic acid and hydrogen peroxide. The resultant hydrogen peroxide is determined electrochemically by suitable detection means, preferably a polarographic cell.

DETAILED DESCRIPTION OF THE INVENTION

Figure 1:
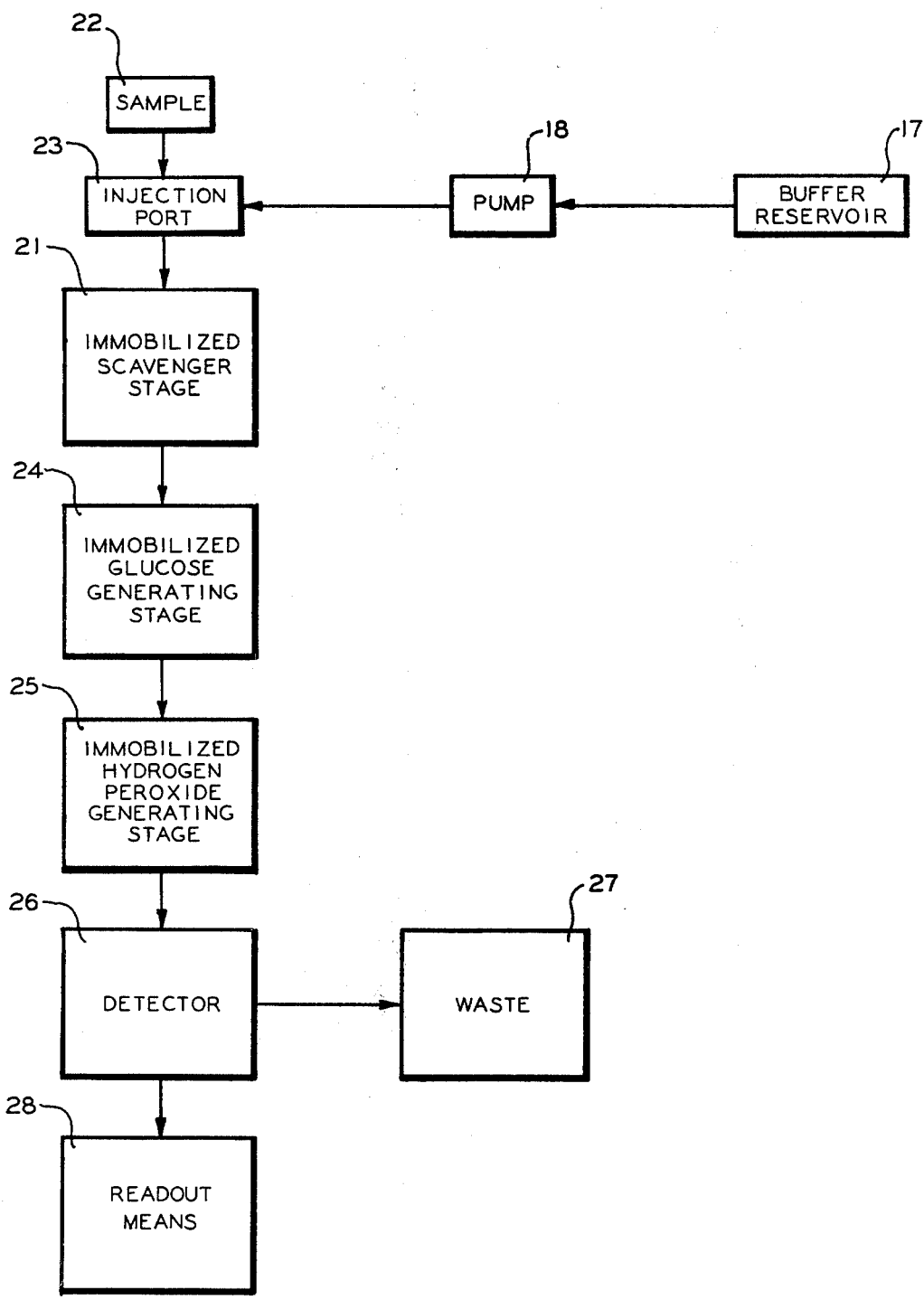
FIG. 1 shows a flow diagram according to the method of the invention with the immobilized reagent stages separated.

The present invention relates to the determination of sugars, particularly the monosaccharide, glucose, and glucose based disaccharides, oligosaccharides and polysaccharides. While the method and apparatus hereinafter described is useful to determine sugars based on monosaccharides other than glucose, it is particularly well suited to a determination of glucose base sugars such as glucose, maltose, maltotriose, and starches such as amylose and amylopectin. As used herein the word sugar is defined to be a monosaccharide, disaccharide, oligosaccharide or polysaccharide which may contain glucose in its structure but need not necessarily contain such glucose.

In many commercially and biochemically important samples, it is desired to measure total free glucose. Sometimes, however, it is desirable to determine the total glucose-based sugars excluding free glucose. For example, such a situation exists in the food industry with infant foods, wherein maltose is a major sugar component of the food preparation. Quality control tests can be performed to monitor the total amount of maltose in the food sample without measuring the free glucose which, for the purpose of the maltose determination, is a contaminating sugar.

Additional areas, where the ability to monitor sugars selectively is desired, are in clinical analysis where blood sugar levels are very important in the diagnosis of disease, and in the brewing industry where sugar content balance must be controlled precisely to produce a flavorful product.

To exemplify the procedures of the invention, a method for the detection of a glucose based sugar will be discussed in detail, it being understood that the method is equally applicable to many glucose-based as well as non-glucose-based sugar, oligosaccharide or polysaccharide, for example maltose, maltotriose, etc.

The method of the invention for the detection of sugars in a fluid sample containing a glucose based sugar and also containing free glucose as an original contaminant in the determination, comprises a unique flow-through combination of immobilized enzymes with a hydrogen peroxide detection means. All of the elements and component stages of the combined flow-through system cooperate in acting upon selected components of the sample being tested to ultimately give a sugar quantification in the fluid sample.

Generally, the method applied particularly for the detection of a sugar in a fluid sample, comprises the initial injection of the sample into a buffered diluent. The buffered sample flows through a scavenger stage wherein contaminating free glucose that may be initially in the sample is removed. The removal of substantially all of the contaminating glucose before the sugar determination is very important. Accordingly, the rate of flow of the sample through the scavenger stage may be adjusted as needed. In the preferred embodiment, the scavenger stage comprises two distinct enzyme reactions comprising the reaction of the glucose with a coimmobilize glucose oxidase-catalase reagent, whereby the glucose is converted to gluconic acid and hydrogen peroxide by the glucose oxidase, and the generated hydrogen peroxide is converted to water and oxygen by the catalase. Because the hydrogen peroxide is the ultimate product resultant from the subsequent sugar reactions, it is necessary to make certain that the hydrogen peroxide is removed and converted to water and oxygen so that it will not produce erroneous results in the detection stage. To assure complete destruction of the hydrogen peroxide, the sample can be passed through additional highly purified catalase stages as needed. Additionally, different loading fractions of the glucose oxidase and catalase in the scavenger stage may accomplish the desired result, if the sample is known to contain very high levels of glucose which would saturate a single, low loading fraction scavenger stage.

The glucose-free and hydrogen peroxide-free sample next flows through an immobilized glucose generating stage wherein the sugar in the sample is reacted with a glucose reagent to generate glucose. In the preferred embodiment of the invention, the glucose generating reagent comprises at least one immobilized enzyme, typically glucoamylase or maltase. In this stage there is a substantial conversion of the sample sugar to produce glucose. In most cases, the maximum conversion rate of sugar to glucose is desired.

The sample containing the generated glucose flows next through a hydrogen peroxide generating stage wherein the generated glucose, resultant from the hydrolysis of the sample sugar is converted to gluconic acid and hydrogen peroxide. The generated hydrogen peroxide in the sample is sensed by a hydrogen peroxide sensitive detection means, which generates a signal which is directly proportional to the concentration of the sugar originally contained in the sample. The detection means is typically a detector in the form of an electrochemical cell. The cell in the preferred embodiment of the invention is a three electrode polarographic electrode as shown in copending application Ser. No. 477,922, filed June 10, 1974.

Reactions Of The Procedure To Detect Sugar:

1. Scavenger Stage.

a. sugar + glucose $\xrightarrow{\text{glucose oxidase}}$ sugar + gluconic acid + $H_2O_2$

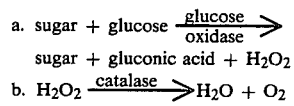

b. $H_2O_2 \xrightarrow{\text{catalase}} H_2O + O_2$

2. Glucose Generating Stage.

sugar + gluconic acid $\xrightarrow{\text{x or y}}$ gluconic acid + glucose

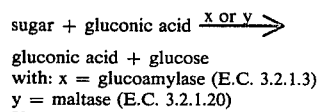

with: x = glucoamylase (E.C. 3.2.1.3)
   y = maltase (E.C. 3.2.1.20)

3. Hydrogen Peroxide Generating Stage.

glucose + $O_2$ + $H_2O$ $\xrightarrow{\text{glucose oxidase}}$ gluconic acid + $H_2O_2$

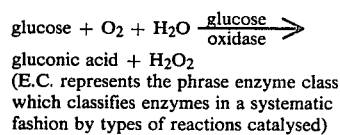

(E.C. represents the phrase enzyme class which classifies enzymes in a systematic fashion by types of reactions catalysed)

Typically, in the determination of a sugar in a sample, the entire reaction procedure is completed within a short time e.g. on the order of about 50–70 seconds, at temperatures ranging from about 0° to about 50° C.

Because the enzymes used in the procedure all catalyze their respective reactions in the 4 to 8 pH range, the sugar prior to contact with the scavenger stage, is diluted by the injection into aqueous diluent which is buffered to prevent the pH of the sample from drifting out of the efficient pH range for use of the enzymes in the method. Preferably, the pH of the buffered diluent is in the range of about 5 to 7 for overall efficiency of the method. Particularly, suitable aqueous buffered diluents are solutions of sodium acetate and acetic acid. Most buffers are acceptable if they have no detrimental effect on the enzyme activity. Suitable buffers, for example, which are acceptably used in the method include sodium citrate, and water soluble phosphate, and phthalate salts in concentrations of about 0.001 to 0.5 M. As will be shown in an example concerning the determination of the maltose and the trisaccharide, maltotriose, the pH is about 5.6 and the acetate about 0.10 M. These are typical values and are well within the ranges given above.

The oxygen required for the oxidation reaction in the hydrogen peroxide generating stage described above is provided by that oxygen concentration which is normally dissolved in the sugar sample specimen and buffered diluent at room temperature. This oxygen concentration usually provides enough oxygen to oxidize sufficient glucose for reliable and reproducible electrochemical detection. It is not necessary for all of the glucose to be oxidized to hydrogen peroxide. It is only necessary that the percentage conversion is reliable and reproducible from a standard to unknown specimens within a given set of laboratory conditions. Thus, for example, partial conversions even on the order of 20% are acceptable to provide precise polarographic response for the purpose of calibration and analysis. In the preferred embodiment, essentially all of the glucose is oxidized to hydrogen peroxide, so that any possible error of variation in conversion from sample to sample is eliminated. To achieve such complete conversion of glucose, supplemental oxygen from an external source (e.g. a sparge of oxygen or an oxygen-containing gas) can be introduced into the specimen if desired, although this is seldom required, since for samples suspected of extremely high concentrations of sugars, the sample size may be reduced.

Slight fluctuations can occur in the dissolved oxygen concentration in the sample and buffered diluent as a function of changes in pressure or temperature. Such fluctuations are minor and the presence of sufficient oxygen is assured when using the detection method, sample size and concentrations herein specified. This is an important advantage over methods measuring glucose as a function of oxygen depletion. Also, increased precision is achieved when measuring hydrogen peroxide as compared to oxygen measurement because extreme sensitive hydrogen peroxide sensors are known, and the fact that in oxygen determinations one measures the difference between a large number and a slightly greater large number. In determining hydrogen peroxide one begins at zero concentration and measures the difference between zero and a larger number, thereby lowering any inherent error in the measurement.

The sample size of a sugar specimen injected into the buffered diluent can be varied with the concentration of sugar in the sample. The sample size should be controlled so that the available oxygen is not depleted, since this would result in the determination of the available oxygen as compared to the desired determination, i.e., the measure of the sugar when oxygen is not a limiting reagent. For physiological fluids such as blood and urine having unknown concentration of sugar within the expected concentration range, dilution of 2.5 microliters of specimen into a stream of buffered diluent flowing at the rate of about 0.1 to 5 and preferably about 0.1 to 2 ml per minute is suitable for a significant polarographic response. Usually, for efficiency and economy, a small sugar specimen (e.g. about 2 to 10 microliters) is injected into a stream of buffered diluent flowing at the rate of about 0.1 to 10 ml per minute for introduction into the bed of immobilized glucose oxidase. A small conventional metering pump can be used to pump the diluent.

In addition to the buffer, it is desirable to add salts such as potassium chloride or sodium chloride which serve to establish a reference potential when silver-silver chloride reference electrodes are used. A bacterial inhibitor can also be incorporated in the buffered diluent to retard bacterial interference.

Scavenger Stage

As stated heretofore, the sample to be tested probably contains some glucose and it is necessary to remove any of the initial contaminating glucose in order to determine the other sugars. In testing biologic samples such as blood, urine, alcoholic beverages or food preparation, substantial amounts of glucose can be present and will give erroneous results if the contaminating glucose is not removed or compensated for in an initial stage, because in subsequent stages, glucose is generated in the present procedure, which is the quantitative equivalent of the sugar present in the sample.

The scavenger stage in accordance with this invention is designed to remove the interfering glucose of the sample, and in the preferred embodiment, comprises the use of coimmobilized enzymes as a reagent which reacts with the interfering glucose and neutralizes it in, or removes it from, the sample. Particularly preferred is a coimmobilized glucose oxidase-catalase reagent wherein the glucose oxidase initially converts the interfering glucose in the sample to gluconic acid and hydrogen peroxide, and the catalase then converts the hydrogen peroxide to water and oxygen. The gluconic acid, water and oxygen are inert species with respect to the detection means in the subsequent detection stage. It is necessary that substantially all the hydrogen peroxide generated from the interfering glucose be removed because hydrogen peroxide is detected in the detection stage from subsequently produced glucose. To assure that all the hydrogen peroxide is removed, the sample can be passed through a second immobilized catalase reagent in the scavenger stage wherein the catalase can be of a highly purified nature, although this is usually not necessary.

Figure 2:
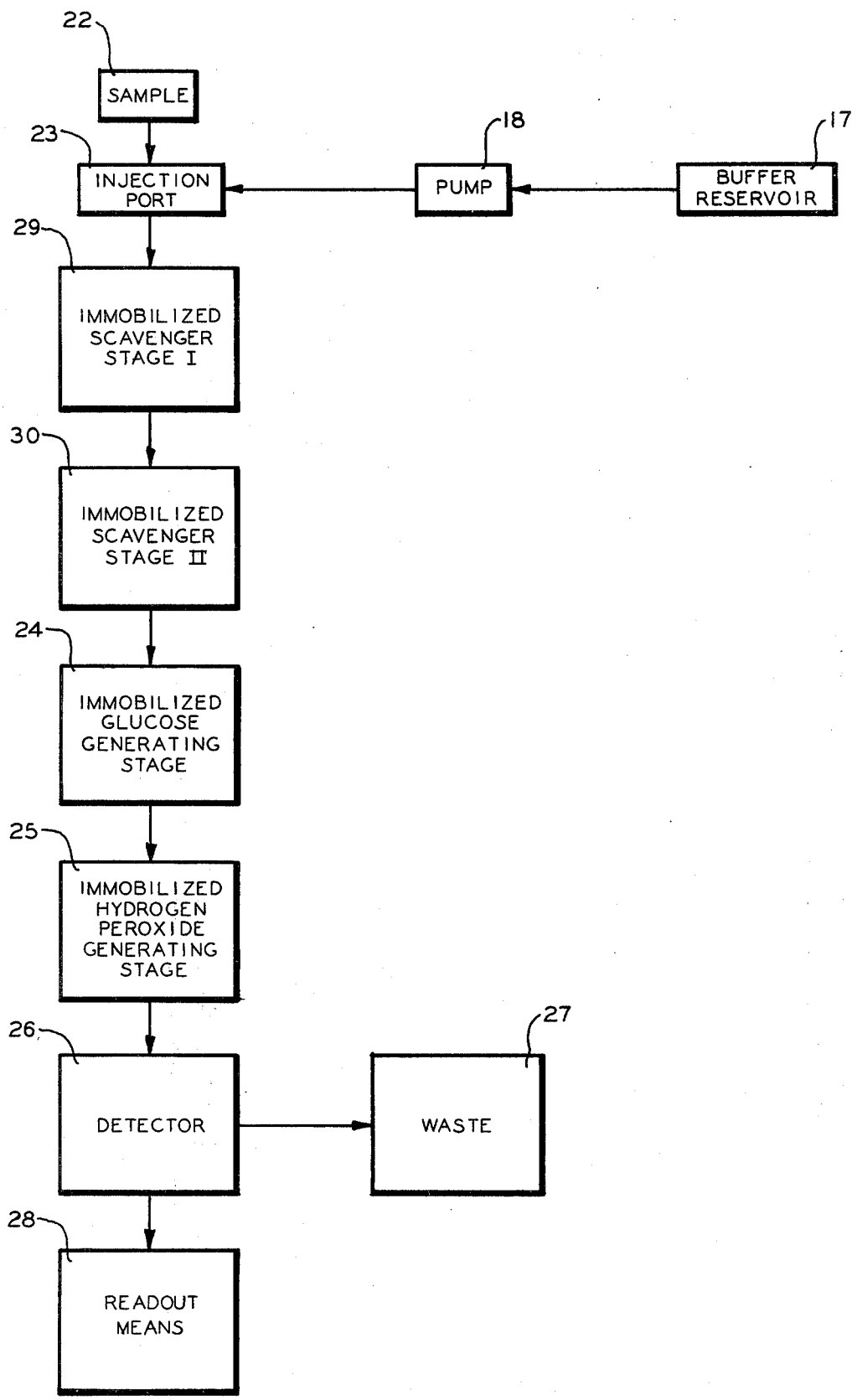
FIG. 2 shows the method of the invention of FIG. 1 with the immobilized scavenger stage separated into two discrete stages.

As will be discussed in detail when reference to the drawings is made in detail, the scavenger stage employs two different enzymes. There are many optional configurations to the scavenger state. In one option, the two enzymes, glucose oxidase and catalase, are coimmobilized so that they are on the same solid support. This option is represented in FIG. 1. FIG. 2 shows the alternative embodiment wherein the two enzymes are separated into two different cartridges. This provides for easy interchange of aging enzymes, i.e. loss of activity, of one type and not another. Also, should alternative enzymes be used this separate stage option would provide for optional adjustment of solution pH between stage so as to pH optimize the solution for the range of activity of the second enzyme.

Immobilized Glucose-Generating Stage.

The sample from the scavenger stage containing the glucose-free sugar flows to an immobilized glucose generating stage wherein the sugar is converted as nearly as possible totally to glucose. The glucose generating reagent must be capable of converting as much sugar to glucose during the flow time as is practically possible. This is accomplished by careful choice and loading of the enzyme, and the enzyme should be suitably immobilized so that it does not leach into the flow stream of the sample.

Several effective glucose generating reagents are available as a reagent in this flow-through procedure. Two of the most useful are the enzymes glucoamylase (E. C. 3.2.1.3) and maltase (E. C. 3.2.1.20). When an instrument is fitted for the continuous monitoring of maltose, the enzyme maltase may be used alone. In a procedure to determine a number of different sugars, oligosaccharides or polysaccharides, the enzyme glucoamylase is used due to its wide substrate effectiveness. The factors involved in selecting the glucose generating reagent are stability, reactivity, ease of handling, and ease of purification. Maltase is presently difficult to purify, when compared to glucoamylase. Glucoamylase on the other hand is able to degrade most naturally occurring disaccharides, oligosaccharides and polysaccharides of interest completely down to glucose, i.e. it hydrolyzes both the α-1,4-, and α-1,6-glucosidic linkages, although its reaction velocity on α-1,6- substrates is somewhat lower on α-1,4-substrates. It has a molecular weight of about 48,000 gm/mole and is stable when immobilized for long periods of time. This enzyme is easy to handle, to purify and is able to react with the sugar from the sample quite effectively.

Hydrogen Peroxide Generating Stage

The glucose generated in the glucose generating stage and the sample next flow to a cartridge which contains immobilized glucose oxidase. The glucose oxidase converts the glucose to hydrogen peroxide and gluconic acid. The glucose oxidase may be purified and immobilized by any of the examples which follow. The resultant hydrogen peroxide then flows to an electrochemical cell which is physically separate from the final immobilized enzyme stage.

With respect to the preferred support to be used in the method of the present invention for immobilizing enzyme reagents, porous particulate alumina has been used with good results as the solid support for all protein immobilizations. The particulate alumina is washed with distilled water after having been sieved with an appropriate size sieve. The particles are usually on the order of about 0.1 to 0.2 microns average diameter, with a high cavity content to increase the loading mass of enzyme per unit mass of support. The support is then preferably air dried, with a final distilled water wash and then placed under 6 M HCl for about two hours. This procedure is believed to activate the alumina to facilitate deposition of the proteins. The activated alumina is again washed and dried. The resultant alumina can be stored under distilled water, a suitable buffer, or used at once.

It was found that the porous particles or the porous matrix having a volume porosity in the range of about 10 percent to 80 percent, and preferably in the range of about 15–50 percent are very suitable for use in the present purposes. The pore size of the support is important in that it should have pores large enough to allow diffusion of the enzyme into the pores to be deposited in the inner surfaces of the particles of the composite. Average pore size diameters of the porous particulates in the range of about 0.01 micron to 10 microns are suitable for most applications with about 0.01 to 2 being preferred for efficiency and economy.

Other porous particulate support can be refractory ceramic oxide powders such as zirconia powder, magnesia powder, silica powder, thoria powder, glass powder, powdered clay, powdered talc, and the like. The particle size of the porous particulates is not critical, although a size range of about −5 to +400 mesh is practical. For efficiency and economy, the size fraction of about −20 to +100 mesh (U.S. Standard Sieve) can be used.

Porous, inert, rigid, dimensionally stable, refractory oxide, fluid permeable, membrane supports can be prepared by compacting refractory oxide powders to form a "green compact" of the desired configuration such as bars, sheets, etc. The green compacts are then fired for a period of time, and at a suitable temperature sufficient for sintering to yield porous, desired refractory supports. The sintering should not be conducted at temperatures or for periods of time which would cause a collapsing or coalescence of the particles to form a nonporous body. A convenient indication of the degree of sintering is a comparison of the actual density of the fired compact as compared to the theoretical density of the oxide being fired. Of the many oxides which can be used for the present purposes, alumina is preferred for its chemical durability and ease of fabrication.

In forming the support from a powdered refractory oxide, a powdered particle size is selected to yield a sintered compact having a porosity and pore size in the range set forth above. The techniques for compacting and sintering of the porous supports are well-known in the art. Generally, the compacting pressures are in the range of about 1,000 psi to 10,000 psi and sintering temperatures are in the range of about 1,000° to 1,700° C. are commercially expedient. Additional details on compacting and sintering of refractory oxides are set forth in the book "Oxide Ceramics", by E. Ryshewitch, published in 1960 by Academic Press, New York, N.Y.

Detection Stage

The hydrogen peroxide generated in the hydrogen peroxide generating stage is passed through a detection means or detector such as a polarographic cell, preferably containing a three electrode system, which furnishes a cell current which is a measure of the hydrogen peroxide under test in the cell and thus of the sugar in the original sample. In copending application Ser. No. 477,922, filed June 10, 1974 there is disclosed a method and apparatus for analysis of glucose by oxidation thereof in a bed of immobilized glucose oxidase. The procedures and detection means set forth herein are incorporated herein by reference and can be used in this detection stage for the generated glucose. In addition, U.S. Pat. No. 3,957,592 discloses an apparatus and method for the measurement of a cell current using a polarographic cell which is suitable and adaptable for use with the procedure herein to measure the generated glucose in relation to the quantitative amount of sample sugar in the original sample.

U.S. Pat. No. 3,902,970 discloses another detection cell usable herein, for the measuring of the concentration of glucose in solution, wherein generated hydrogen peroxide is measured in an amperometric cell. The cell has a small bore flow path and includes a cylindrical measuring electrode which carries the sample through its relatively long narrow bore, a counter electrode, reference electrode and a differential amplifier for automatically adjusting the current between the counter and measuring electrodes to maintain the potential between the two electrodes at a predetermined value as fed to one input to the amplifier. The current from the measuring electrode is measured as an indication of the concentration of hydrogen peroxide in the solution and thus the glucose concentration.

In addition to the use of amperometric type detection cells, other suitable types of detection means can be used herein for the measurement of the generated hydrogen peroxide. In particular, a spectrophotometer can be used herein as the detection means for measuring the generated hydrogen peroxide as set forth hereinafter.

Apparatus For Determining Sugars

In FIG. 1, the schematic representation of the apparatus has a buffer reservoir 17 which feeds into a pump 18. The pump 18 is connected to an immobilized scavenger stage 21 which contains immobilized glucose oxidase and catalase.

The sample 22 of the sugar is injected into the injection port 23 which is connected to the scavenger stage 21. In the embodiment of FIG. 1, the scavenger stage communicates with an immobilized glucose generating stage 24. In this embodiment the glucose generating stage 24 communicates with the hydrogen peroxide generating stage 25.

The hydrogen peroxide generating stage communicates with the detection means which is an electrochemical detector 26.

The sample leaves the detector 26 and is vented to a waste reservoir 27. The electrical signal from the detector stage 26 is then displayed at the readout means 28.

In the embodiment of FIG. 1 each of the immobilized enzyme stages, 21, 24, 25 is a separate cartridge for ease of single cartridge interchange or replacement. In the embodiment of FIG. 2, the scavenger stage is subdivided into two separate stages, stage I, 29, and stage II, 30. This splitting up of the glucose oxidase stage, stage I, and the catalase stage, step II, facilitates ease of replacement with fresh enzyme or alternative choices of reagents.

Figure 3:
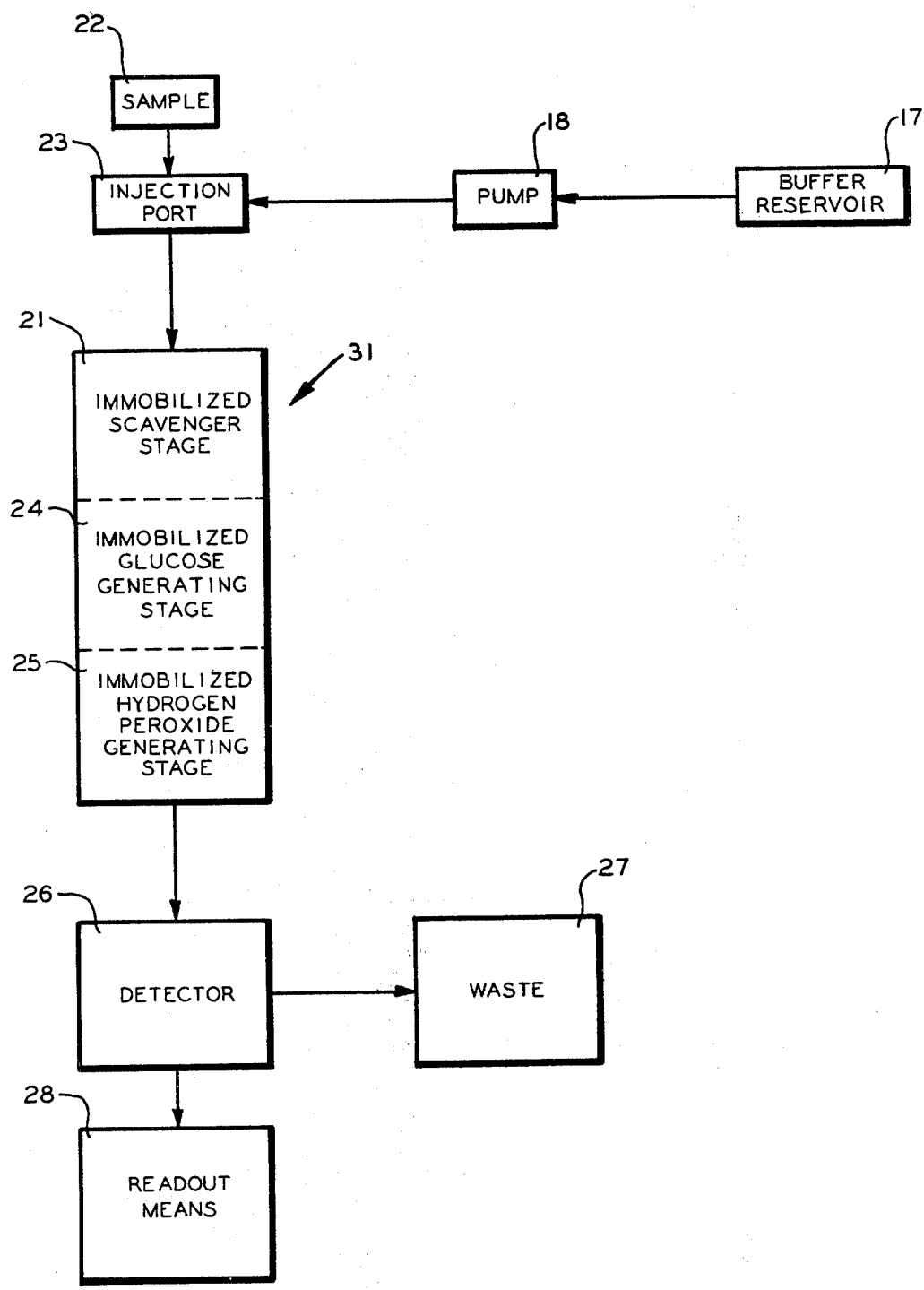
FIG. 3 shows the method of the invention of FIG. 1 with all immobilized reagents in a single stage.

In the alternative embodiment shown in FIG. 3, the three stages 21, 24, 25 are all combined into one combination cartridge 31 so that the instrument may be constructed to hold only one cartridge.

Immobilized Reagents

The various reagents reacting with the sample containing sugar such as maltose are in the preferred embodiment, all immobilized in the various stages. Any of the known methods for immobilizing the enzyme reagents on an insoluble support to form a bed of immobilized reagent can be used in this invention. For example, the glucose oxidase in the scavenger and hydrogen peroxide generating stage can be covalently coupled to a porous glass or alumina support with an amino-functional silane coupling agent as disclosed in the article entitled "Immobilized Enzymes: A Prototype Apparatus For Oxidase Enzyme In Chemical Analysis Utilizing Convalently Bound Glucose Oxidase", by M. K. Seibel et al appearing in Analytical Biochemistry, 52, 402-414 (1973); glucose oxidase can be immobilized on column packing as in the article entitled, "A New Principle Of Enzymatic Analysis" by H. V. Bergmeyer and A. Hagh appearing in Z. Anal. Chem. 261, 333-336 (1972). Other immobilization techniques are known in the art.

In the scavenger stage, as shown in FIG. 1 and 3, the glucose oxidase and catalase in series may be coimmobilized on a suitable support in a flow-through cartridge by the above methods. As state previously, a second cartridge can be used in a subsequent scavenger stage. Similarly, enzymes in the glucose-generating stage, the glucoamylase or maltase can be immobilized as set forth hereinafter.

Preferably, the enzyme reagents of this invention are immobilized by cross-linking them onto porous acid-activated alumina because these immobilization techniques have been well developed and their ease of operation are well-known. Alumina exhibits high durability with moderate reagent-load capacity, allowing the high flow-rates required for fast analysis of samples in the flow-through procedure of the invention.

In addition, the following patents disclose various immobilization techniques for use in this invention: U.S. Pat. No. 3,933,589 issued to Melvin H. Keyes, Jan 20, 1976 entitled "Chemical Immobilization of Enzymes"; U.S. Pat. No. 3,839,175 issued to Melvin H. Keyes, Oct. 1, 1976 entitled "Electrodeposition of Enzymes"; and U. S. Pat. No. 3,860,486 issued to Melvin H. Keyes et al, Jan. 14, 1975 entitled "Immobilizing Enzymes With Polystyrene Derivatives". The disclosures of these references are incorporated herein by reference. Thus, in forming the bed of immobilized enzyme the selection of the support from materials such as porous glass, particulate and preferably porous refractory oxides such as alumina, titania, zirconia, silica, magnesia, talc, and thoria; glass frit; particulate porcelain; compacted and sintered refractory oxides; clays; water-insoluble polymers; and immobilizing the enzyme thereon by chemical or physical means is well known in the art.

The immobilization of the reagents on an inorganic support, particularly alumina, is preferred because a non-compressible support gives high flow rates for the samples flowing through the analyzer, is less time consuming, etc.

With respect to the columns, the important requirement is that the packed column be permeable to the sample specimen while providing a high surface area to volume ratio to assure adequate contact between the enzyme or other reagent and the sample specimen.

Having described the method and apparatus of the present invention in detail with regard to a sample unknown containing sugar, such as maltose, the following other known uses are described in general.

Also high molecular mass starches such as amylose and amylopectin may be determined using the method and apparatus of the present invention. Referring to FIG. 1, in this case the starch, with any contaminating glucose, would be dissolved into solution and injected as sample 22 into injection port 23. The starch flows into the immobilized scavenger stage 21 wherein contaminating glucose is removed. The glucose free sample flows next into the immobilized glucose generating stage 24 wherein the starch structure is hydrolyzed to produce glucose. The flow rate of the buffer stream must be adjusted to allow for sufficient conversion while the sample is in the immobilized glucose generating stage 24 to yield analytically reliable results. The resultant glucose flows to the hydrogen peroxide generating stage 25 where it is converted to gluconic acid and hydrogen peroxide. The sample then flows to the detector 26 wherein the hydrogen peroxide is measured. The flowing buffer stream is vented to waste 27 and the signal from the detector 26 is conditioned and displayed by readout means 28.

It has been found that some starches are either water insoluble or are soluble but of such a composition that they will cause flow irregularities in the stream of flowing buffer solution. In these cases, the starch may be prehydrolyzed before being injected into the apparatus in a starch hydrolysis stage. It has been found that soluble or immobilized glucoamylase may be mixed with the sample before it is injected. This allows for the partial degradation of the starch chains so that they will not cause flow irregularities in the apparatus.

However, when one deals with these problem samples the glucoamylase may produce substantial amounts of free glucose during the starch prehydrolysis treatment. Therefore, the sample must be injected at a point between the scavenger stage 21 and the glucose generating stage 24. To determine the amount of glucose, the starch plus glucose sample is run bypassing the scavenger stage 21. Then the sample is run after the starch has been removed by microfiltration, also by bypassing the scavenger stage 21. The difference of the two valves represents the free glucose in the sample.

Also, it is understood that if one desired to determine the presence and/or concentration of a sugar like the disaccharide sucrose (made from one glucose and one fructose molecule) or would simply substitute a sucrose hydrolase for maltase or glucoamylase, and again measure the resultant glucose as a measure of the sucrose in the sample. Here also, the scavenger stage would be very important since glucose is produced as the measurable species generated by the sugar sample.

Similarly, to detect a nonglucose based sugar one would simply include in the glucose generating stage a hydrolase and an isomerase or transferase to hydrolyze the sugar into its constituent molecules and then convert one or more of the constituent molecules to glucose to supply the hydrogen peroxide generating stage.

The following Examples further illustrate the invention and disclose the preparation of the various immobilized reagents used in the several stages of the sugars determination procedure.

EXAMPLE 1

PREPARATION OF THE SCAVENGER STAGE (GLUCOSE OXIDASE)

1. Twenty grams of 35 percent porosity, −50 to +60 meshed porous alumina having an average pore size of one-tenth micron, is carefully weighed out.
2. The porous alumina is then washed under 25, 250 ml aliquots of distilled, deionized water.
3. The washed alumina, from step 2, above, is then placed under 150 ml of six normal hydrochloric acid in a 200 ml erylenmeyer flask, for one to one and one-half hours, swirling gently every ten minutes at room temperature.
4. During the acid-activation of the porour alumina discussed in step 3, above, the following solutions are prepared:
   a. A 30 to 40 ml length of dialysis tubing (Spectrapor, trademarked by Spectrum Medical Laboratory) having a molecular weight cut-off limit of 6,000 to 8,000, is obtained and placed in a 200 ml breaker, under 150 ml of 1/100 molar maleate buffer, pH 5.6, and refrigerated at 0° C. to 4° C. for one-half to one hour.
   b. A cross-linking solution is prepared by dissolving two grams of CMC, i.e., 1-cyclohexyl-3(2-morpholinethyl)-carbodiimide metho-p-toluene sulfonate into ten milliliters distilled, deionized water, and allowed to stir one hour, at room temperature.
   c. Twenty milliliters of glucose oxidase (Miles Research Laboratories, Code #31617) is measured out, and is activated by adding twenty-six milligrams succinic anhydride. The resulting mixture is allowed to react for at least forty minutes at room temperature.
5. At the end of the acid-activation time indicated in step (3), above, the alumina is rinsed by rapid swirling under three, one-hundred fifty milliliters aliquots of distilled, deionized water.
6. The alumina is then placed under one-hundred fifty milliliters distilled, deionized water, and deaerated for one hour at room temperature. The flask is swirled gently every ten minutes.
7. At the end of step (6), above, the supernatant solution is carefully decanted off, and discarded. To the alumina remaining is added the solution prepared in step 4(b) above.
8. A knot is tied in one-end of the dialysis tubing from step 4(a), above.
9. Into the dialysis bag is added the mixture described in step (7) above.
10. Then the solution prepared in step 4(c), above, is also added to the dialysis bag, and the open end is then sealed by tying a knot.
11. The closed dialysis bag containing the reactants from step (10), above is then placed under one-hundred fifty milliliters, distilled, deionized water in a two-hundred milliliter flask. This breaker is then placed on a laboratory shaker water bath at zero to six degrees centigrade for twelve to sixteen hours.
12. After step (11), above, the material is removed from the dialysis bag, and is washed under one liter distilled, deuibuzed water, and it refrigerated at 0° C. to 4° C. under ten milliliters of one-one-hundredth molar maleate buffer, pH 6.
13. The activity of the final product is measured: Glucose oxidaze activity is measured in a $5 \times 10^{-2}$ M beta-d-glucose (Sigma Chemical Company) solution, buffered to pH 5.6 with 0.01 M acetate buffer. The glucose oxidase activity is found to be 69 U per ml of porous alumina-enzyme composite.

EXAMPLE 2

PREPARATION OF THE TWO-STAGE SCAVENGER REAGENT

A. Preparation of Immobilized Glucose Oxidase

1. Thirty grams of −60+70 meshed porous alumina is weighed out, and sieved through an eight mesh wire screen for five minutes. The sieved alumina is then washed under distilled, deionized water until the supernatant is clear.
2. The washed alumina is then placed under 200 ml of six normal hydrochloric acid for one hour.
3. Into distilled, deionized water is dissolved sufficient crude glucose oxidase (Sigma Chemical Co.) to make a solution of absorbance 1.50 at 450 nm. The pH of this enxyme solution is adjusted to pH 7.5.
4. Ten milligrams succinic anhydride is dissolved in one milliliter of spectral grade acetone.
5. One-tenth milliliter of the solution prepared at step 4, above, is added to the enzyme solution of step 3, above, every ten minutes. A 20-minute reaction period is allowed after the final tenth of a milliliter of the solution prepared on step 4, above, has been added.
6. The acid-activated alumina from step 2, above, is then washed with distilled, deionized water until the supernatant is clear.
7. The washed alumina is placed under 200 ml distilled, deionized water, and deaerated for one hour.
8. The activated glucose oxidase from step 5, above, is added to the deaerated alumina of step 7, above, and the pH is immediately adjusted to pH 4.2.
9. One tenth gram EDC, i.e., 1-ethyl-3-(3-dimethylaminopropyl)-carbodiimide hydrocloride is added to the solution prepared in step 8, above.
10. Four-tenths of a gram EDC is dissolved in 30 ml distilled, deionized water.
11. The solution prepared in step 10, above, is added to the solution of step 9, above, at a rate of 1/10 ml per minute.
12. The reaction of the materials prepared in step 11, above, is allowed to continue undisturbed, at 0° C. to 5° C., on the laboratory shaker, for 12 to 16 hours.
13. The final product is washed with 2 liters, 2/10 molar ammonium sulfate, followed by 4 liters distilled, deionized water. The material is then stored under 10 to 20 ml distilled deionized water at 0° C. to 4° C.
14. The activity of this preparation is found to be:

a. The activity of glucose oxidase, in a 1/100 molar beta-d-glucose (Sigma Chemical Co.) solution, buffered to 1/100 molar acetate, pH 5.6 is measured as 57 Units per milliliter of alumina-glucose oxidase composite.

b. The activity of catalase, prepared by these same procedures is, in a 5/100 percent hydrogen peroxide solution, buffered as in 14a, above, is measured as 18 Units per milliliter of alumina-glucose oxidase composite, due to residual catalase which is present in the glucose oxidase which is used.

B. Preparation Of The Immobilized Catalase

1. Thirty grams −70+80 mesh porous alumina is weighted out, and washed by hand swirling with distilled, deionized water, until the supernatant is clear. The washed alumina is then rinsed by hand swirling with 15, 200 ml volumes of 1/10 molar hydrochloric acid.

2. The washed alumina from step 1, above, is then placed under 250 ml of six normal hydrochloric acid for one and one half hours at room temperature (approximately 27° C.).

3. The acid-activated alumina is then decanted of the six normal hydrochloric acid supernatant, and rinsed with two, 250 ml volumes of 1/10M hydrochloric acid.

4. The rinsed acid-activated alumina is then placed under 200 ml 1/10 M hydrochloric acid, and deaerated at room temperature, swirling every five minutes, for one hour.

5. The supernatant above the deaerated alumina is decanted off, and discarded.

6. The alumina is then placed under 250 ml of 1/100 M acetate buffer, pH 5.5 and is allowed to swirl, undisturbed on the laboratory shaker for at least one hour.

7. Using an omega amino n-decyl hydrophobic column (MilesYeda, Ltd.), having a radius×length=1.3 cm×38.0 cm, ten grams crude glucose oxidase dissolved in 25 ml distilled, deionized water, dialyzed against a one millimolar phosphate buffer, pH 6, that is 3/100 millimolar in sodium cyanide, is eluted at a flow-rate of ten to 15 ml per hour. The fraction collected in test tube numbers I and II having a total volume of about 30 ml is slected for immobilization.

| Test Tube No. | Activity (U/mg) | |
| --- | --- | --- |
| | Glucose Oxidase[a] | Catalase[b] |
| I | 7.7 | 50.0 |
| II | 10.0 | 62.4 |

[a]Glucose oxidase activity is measured in a 1/100 molar beta-d-glucose solution, buffered to 1/100 molar acetate buffer, pH 5.6.
[b]Catalase activity is measured in a ½% hydrogen peroxide solution, buffered as in (a), above, at pH 5.6.

8. The material of step 7, above, is added to the solution of step 6, above, and is allowed to react, undisturbed, on the laboratory shaker, at 0° C. to 6° C. for at least ½ hour.

9. During the adsorption indicated in step 8, above, add to 50 ml of 5/100 molar phosphate buffer, pH 6,
 (a) ten milliliters spectral grade methanol
 (b) 2/10 milliliter diaminopropane
 (c) 1/100 milliliter dibromoethane
 (d) 15/100 milliliter concentrated hydrochloric acid, and allow to stir undisturbed on a magnetic stirrer for half hour, at room temperature.

10. The contents from step 9, above, is added to the contents of step 8, above, in equal volume aliquots, over a half hour period.

11. The mixture prepared in step 10, above, is allowed to react for 12 to 16 hours, at 0° C. to 4° C. on the laboratory shaker.

12. The final product is washed under two liters, 1/100 M acetate buffer, pH 5.5, which is 1/10 molar in sodium chloride followed by a two liter wash with distilled, deionized water.

13. The washed final product is then stored under 15 ml 1/100 M acetate buffer, pH 5.5, that is 3/100 millimolar in sodium cyanide.

14. The activity of this material in an 88 mM hydrogen peroxide, 0.01 M acetate, pH 5.5 substrate-buffer solution is measured as 59 Units of catalase per milliliter of the alumina-catalase composite, with negligible glucose oxidase activity.

EXAMPLE 3

PREPARATION OF THE SCAVENGER STAGE (CATALASE)

a. Twenty to thirty grams of −70+80 mesh porous alumina, used above is weighed out; and is washed under distilled, deionized water until free of fines. This is followed by a 1 liter rinse with 1 normal hydrochloric acid (Lehigh Valley Chemical Company). This acid-rinsed alumina is then placed under 250 to 500 milliliters of 9 normal hydrochloric acid for 1.5 to 3 hours.

b. At the end of this time, the acid-activated alumina is rinsed with 1 liter of 1 molar hydrochloric acid. The acid rinsed acid-activated alumina is then placed under 0.10 normal hydrochloric acid, and the alumina is evacuated by air vacuum aspiration for one to two and a half hours.

c. The evacuated acid-activated alumina is then rinsed with 1 liter, 0.01 molar acetate buffer, pH 5.5±0.2 and placed under 100 milliliters of 0.01 molar acetate buffer, pH 5.5±0.2, and is allowed to swirl on the laboratory shaker, at 0° C. to 4° C. for 0.5 hour.

d. A quantity of crude glucose oxidase (E.C.1.1.3.4., from Aldrich Chemical Company) is chromatographed on an omega n-decyl amino alkyl hydrophobic gel by a procedure similar to Example 2B. The eluant is a 1 mM phosphate buffer pH 6.0. The first eluted peak is collected, and retained for immobilizatin and is added to the final mixture in step c., above. This mixture was allowed to swirl gently on the laboratory shaker for an additional 0.5 hour.

e. A cross-linking solution is prepared, by adding to 10 ml of spectral quality methanol (Burdick and Jackson) placed in a 100 ml beaker, the following reagents in the order indicated:

1. two-tenths of a milliliter of diaminopropane (Aldrick Chemical Company).

2. One-tenth of a milliliter of dibromoethane (Aldrich Chemical Company).

3. Fifteen-hundredths of a milliliter of concentrated hydrochloric acid (Lehigh Valley Chemical Co.), and 4. Fifty milliliters of 0.01 molar acetate buffer pH 5.5. The cross-linking solution is then allowed to stir for 0.5 hour on a magnetic stirrer.

f. The contents of step e., above are then added to the final contents of the mixture in step d., above; slowly over a 0.5 hour period. The mixture is then allowed to react overnight at 0° C. to 5° C., while swirling on the lab shaker, (in a water bath).

g. The next day, the final product is washed under 2 to 3 liters of 0.01 molar acetate (0.1 molar in sodium chloride, the sodium chloride from Matheson, Coleman and Bell Manufacturing Chemists, Inc.) pH 5.5. The washed product is then stored under 10 to 15 ml of this same buffer, under refrigeration at 0° C. to 4° C.

h. The activity of this material in an 88 mM hydrogen peroxide, 0.01 molar acetate, pH 5.5 susbstrate-buffer solutin is measured by following its increase in oxygen content as a function of time, after the immobilized enzyme is first added to 5 ml of the buffer solution, and the substrate quickly added. Using this procedure the activity is measured as 58.46 U of catalase per milliliter of the alumina-catalase composite.

EXAMPLE 4

IMMOBILIZATION OF THE GLUCOSEGENERATING REAGENT

Twenty-five to fifty grams of porous remeshed alumina, $-50+60$ mesh, was weighed out, washed thoroughly and acid-activated as above. The resulting activated material was placed under 50 ml of 0.01 to 0.05 M acetate buffer, pH 5.6, and set aside for 0.5 to 1.0 hour while gently swirling on the laboratory shaker, at: either (1) room temperature, or (2) 0° C. to 4° C.

During this time 5 to 1500 mg of, (1) crude enzyme (maltase or glucoamylase) (Sigma Chemical Co.) was weighed out, and dissolved in 25 ml of distilled, deionized water, or buffer and centrifuged at 10,000 g's for 0.5 hour, or (2) a 40% ammonium sulfate precipitate was collected. In the case of the crude enzymes, the supernatant solution (at least 25 ml) was added to the acid activated alumina, and allowed to adsorb 0.5 to 1.5 hour. In the case of the 40% ammonium sulfate precipitation, however, the precipitate was redissolved in at least 25 ml of distilled, deionized water, or buffer (0.01 M acetate, pH 5.6), and allowed to adsorb onto the acid-activated alumina for 0.5 to 1.5 hour.

After the adsorption process had been completed, a cross-linking reagent composed of diaminopropane and dibromoethane as in Example 3 was prepared and added. The reaction was allowed to continue overnight, at room temperature, while swirling on the laboratory shaker. Washing and storage is as above, in Example 3.

EXAMPLE 5

PREPARATION OF IMMOBILIZED PURIFIED GLUCOAMYLASE

1. Twenty grams $-70+80$ mesh, rescreened, porous alumina is weighed out, and first washed under distilled, deionized water until free of fines, and then washed under 500 ml, 1/10 M hydrochloric acid.

2. Fifty grams crude glucoamylase is dissolved in 100 ml of 1/100 M phosphate buffer, pH 6, and centrifuged at 12,300 gravity forces for one hour in a ultra centrifuge. The resulting supernatant is decanted off and saved. The resulting insoluble precipitate is discarded.

3. The supernatant from step 2, above, is chromatographed on a Sephadex G-100 (Pharmacia Fine Chemicals) column (6 cm × 120 cm) at a flow-rate of 136 ml per hour. The entire second peak fraction eluting off is selected for immobilization.

4. The washed alumina of step 1, above, is then placed under 250 ml of 9 normal hydrochloric acid and is allowed to swirl, undisturbed, at room temperature for one and one-half hours.

5. The alumina is then washed twice, under 500 ml of 1/10 M hydrochloric acid followed by a 500 ml aliquot wash of 1/100 M phosphate buffer, pH 6.

6. The washed alumina is then placed under 50 ml of 1/100 M phosphate buffer, pH 6 and is allowed to swirl, undisturbed, for at least one-half hour at room temperature on a laboratory shaker.

7. To the mixture prepared in step 6, above, is added the entire contents of step 3 above.

8. The mixture prepared in step 7, aove, is allowed to swirl undisturbed for one hour, at room temperature.

9. Into 15 ml 1/100 M phosphate buffer, pH 6 is added.
  a. five milliliters spectral quality methanol
  b. 5/100 ml diaminopropane c. 2/100 ml dibromethane, and
  d. 5/100 ml concentrated hydrochloric acid.

10. The cross-linking mixture prepared in step 9, above, is added to the mixture of step 8, above, in equal volume aliquots over a half hour period.

11. The resulting mixture from step 10, above, is then allowed to react for 12 to 16 hours, at room temperature.

12. The final product is washed, and stored as in step 11 of Example 7.

13. The activity of this preparation is measured as 8.0 Units of glucoamylase per milliliter alumina-glucoamylase composite, in a 1/100 M maltose substrate solution, buffered to 1/100 M in acetate buffer, pH 5.5.

EXAMPLE 6

PREPARATION OF IMMOBILIZED CRUDE GLUCOAMYLASE

1. Thirty grams, $-70+80$ mesh, porous alumina is weighed out, and washed under distilled, deionized water until the supernatant is clear.

2. This wash if followed by a rinse under one liter of one normal hydrochloric acid.

3. The washed alumina is then placed under 250 ml of 9 normal hydrochloric acid for 1½ hours.

4. The material of step 3, above, is then rewashed as in step 2, above.

5. The alumina is then placed under 250 ml 1/10 M hydrochloric acid, and deaerated for one hour.

6. The alumina is then washed under one liter 1/100 M acetate buffer, pH 5.5, and placed under 100 ml of the same buffer, and allowed to swirl on the laboratory shaker, undisturbed for one-half hour. at 0° C. to 4° C.

7. The enzyme solution is prepared by,
  a. dissolving 6 grams crude glucoamylase into 100 ml 1/100 M phosphate buffer, pH 6 over a one-half hour period to ensure that a good suspension is made.
  b. This material is then centrifuged at 375 gravities for half hour.
  c. The resulting supernatant is decanted off, and saved. The resulting insoluble precipitate is discarded.
  d. The supernatant is filtered through a 2/10 micron pore uncoated filter (Millipore Corporation), with a handpump filter unit (Antilia$^{TM}$ Hand Pump); and
  e. Ten milliliters of this filtered glucoamylase is retained for immobilization.

8. The material from step 7 e, above, is added to the mixture prepared in step 6 above. 9. The procedure is the same as for step 8 to step 12, of Example 5.

10. The activity of this preparation is measured as 9.0 Units of flucoamylase per milliliter of alumina-glucoamylase composite, in a one hundredth molar maltose substrate solution, buffered to one-hundredth molar acetate buffer, pH 5.5.

EXAMPLE 7

NOTE: After the enzyme in step 2, has been suspended, and prior to refrigeration, each sample is centrifuged at 10,000 revolutions per minute (12,350 gravities), for ½ hour. The supernatant is decanted off, and retained for immobilization, while the precipitate is discarded.

PREPARATION OF IMMOBILIZED GLUCOAMYLASE.

(Biological Source: *Aspergillus oryzae*)

1. Twenty-eight grams of prewashed, minus forty plus fifty meshed, porous alumina is weighed out, and placed under six normal hydrochloric acid, for 1½ hour at room temperature, swirling the contents every 15 to 20 minutes.
2. 250 mg crude glucoamylase (Sigma Chemical Co.) is weighed out, and dissolved (suspended) in 25 ml, 5/100 molar acetate buffer, pH 5.5, and refrigerated at 0° C. to 4° C. until ready to use.
3. The material of step 1., above, is then rinsed under four aliquots of distilled, deionized water. Each aliquot of water is 250 ml. It is then deaerated under 150 ml of 5/100 molar acetate buffer, pH 5.5 for one hour, at room temperature.
4. The supernatant of step 3, above, is then decanted off and discarded. The remaining alumina is placed under 50 ml of 5/100 molar acetate buffer, pH 5.5.
5. The solution from step 4, above, is then placed in a cold water bath, on a laboratory shaker, at 0° C. to 4° C., and is allowed to shake undisturbed for at least ½ hour.
6. While step 5, above, is going on, dissolved into 25 ml of distilled, deionized water, two-and-a-half grams CMC, i.e., 1-cyclohexyl-3(2-morpholinethyl)-carbodiimide metho-p-toluene sulfonate.
7. The solution prepared in step 6., above, is then allowed to stir gently for 45 minutes, at room temperature (at about 27° C.).
8. To the material of step 5, above, is added the contents from step 2, above. The mixture is then allowed to adsorb undisturbed, for at least one-half hour at 0° C. to 4° C.
9. At the end of the adsorption time indicated in step 8, above, the solution from step 6, above, is added by pump to the solution of step 8, above. The addition of a cross-linking solution as in Example 5, step 9 is at a rate of 5/100 to 1/10 milliliter per minute.
10. The mixture of step 9, above, is then allowed to react for 12 to 16 hours, at 0° C. to 4° C.
11. The final product, is then washed with three, 250 ml volumes of 15/100 molar ammonium sulfate, followed by three, 250 ml volumes of distilled, deionized water. The final washed material is then stored under 10 ml, 5/100 molar acetate buffer, pH 5.5, under refrigeration at 0° C. to 4° C.
12. The activity of this immobilized glucoamylase is measured as 7.8 units per milliliter of alumina-glucoamylase composite, in a 1/100 molar maltose solution, in 1/100 molar acetate buffer pH 5.5.

EXAMPLE 8

PREPARATION OF IMMOBILIZED MALTASE (Biological Source: *Aspergillus niger*)

1. Twenty-six grams of prewashed, minus 40 plus 50 meshed, porous alumina is weighed out, and placed under six normal hydrochloric acid, for one-and-a-half hours, at room temperature, swirling the contents every 15 to 20 minutes.
2. Two hundred and seventy-five mg of crude maltase (Sigma Chemical Co.) is weighed out, and dissolved (suspended) in 25 ml of 5/100 acetate buffer, pH 5.5, and refrigerated at 0° C. to 4° C. until ready to use.
3. The material of step 1, above, is then rinsed under four aliquots of distilled, deionized water. Each aliquot of water is 250 ml in volume. It is then deaerated under 150 ml of 5/100 molar acetate buffer, pH 5.5., for one hour, at room temperature.
4. The supernatant of step 3, above, is decanted off and discarded and the remaining alumina is placed under 5 1 ml of 5/100 molar acetate buffer, pH 5.5.
5. The solution from step 4, above, is then placed in a cold water bath, on a laboratory shaker, at 0° C. to 4° C., and is allowed to shake undisturbed for at least one-half hour.
6. While step 5, above, is in process, dissolve into 25 ml of distilled, deionized water, two-and-a-half grams CMC, i.e. 1-cyclohexyl-3(2-morpholinethyl)-carbodiimide metho-p-toluene sulfonate.
7. The solution prepared in step 6, above, is then allowed to stir gently for 45 minutes on a magnetic stirrer, at room temperature.
8. To the material from step 5, above, is added the contents of step 2, above. The mixture is allowed to adsorb (react) undisturbed for at least one-half hour at 0° C. to 6° C. on the laboratory shaker.
9. At the end of the adsorption time indicated in step 8, above, the solution from step 6, above, is added by pump to the solution of step 8, above. The addition takes place at a rate of 5/100 to 1/10 ml per minute.
10. The mixture of step 9, above, is then allowed to react for 12 to 16 hours, at 0° to 6° C.
11. The final product, is then washed with three 250 ml volumes of 15/100 molar ammonium sulfate, followed by three 250 ml volumes of distilled, deionized water. The final washed material is then stored under 10 ml 5/100 molar acetate buffer, pH 5.5., under refrigeration at 0° to 4° C.
12. The activity of this immobilized maltase reagent is measured as 10.3 Units per ml of alumina-maltase composite, in a 1/100 molar maltose solution, buffered to 1/100 with acetate buffer, pH 5.5.

EXAMPLE 9

PREPARATION OF THE HYDROGEN PEROXIDE GENERATING REAGENT

1. Thirty grams −60+70 meshed, resieved through an eighty mesh wire screen for five minutes, porous alumina is carefully weighed out, and washed under one liter distilled, deionized water.
2. The alumina is placed under 200 ml of six normal hydrochloric acid for one hour while swirling, undisturbed for one hour.
3. glucose oxidase is prepared as in step 8 of Example 2A.
4. Ten milligrams of succinic anhydride is dissolved in 1 ml of acetone.
5. Three-tenths milliliter of the solution prepared in step 4, above, is added to the enzyme solution of step 3, above, every 10 minutes, and allowed to react undisturbed for 20 minutes after all the solution of step 4, above has been completely added.

6. The material of step 2, above, is then washed under distilled, deionized water, until the supernatant is clear.

7. The alumina is then placed under 200 ml distilled, deionized water and deaerated for at least one hour. The supernatant solution is then discarded.

8. The solution of step 5, above, is then added to the alumina of step 7, above, and the pH is adjusted to 4.2.

9. One-tenth gram EDC, i.e., 1-ethyl-3-(3-dimethylaminopropyl) carbodiimide hydrochloride is added to step 8, above. After a half hour reaction period, the pH is adjusted to 5. with sodium hydroxide.

10. Four-tenths of a gram of EDC, is dissolved in 30 ml distilled, deionized water, and added to step 8, above, at a rate of 1/10 ml per minute.

11. The solution of step 10, above, is allowed to react for 12 to 16 hours, on the laboratory shaker, undisturbed at 0° C. to 5° C.

12. The final product is washed and stored as in Example 2A, step 13.

13. The activity of this preparation is measured as 24 Units glucose oxidase per milliliter alumina-glucose oxidase composite, in a 1/100 molar acetate buffer-substrate solution, pH 5.5, with no detectable amounts of catalase activity.

EXAMPLE 10

PREPARATION OF THE HYDROGEN PEROXIDE GENERATING STAGE

1. Twenty grams, −70 to +80 meshed alumina is washed under two liters distilled, deionized water until free of fines, or the supernantant remains clear, in ten, 250 ml aliquots.

2. The washed alumina of step 1, above, is placed under 250 ml six normal hydrochloric acid for one hour at room temperature.

3. One hundred mg glucose oxidase (Biological source: *Aspergillus niger*, Worthington Biochemical Corporation) is dissolved in 50 ml of a 3/10 molar solution of sodium chloride. The pH is adjusted carefully to pH 4.0 with a one normal solution of hydrochloric acid.

4. Ten milligrams of succinic anhydride is added to the solution prepared in step 3, above, and is allowed to react, while stirring gently for 40 minutes at room temperature. 5. The acid-activated alumina of step 2, above, is washed by hand swirling in a 500 ml vacuum flask with distilled, deionized water, until the supernatant is clear.

6. The washed alumina from step 5, above, is placed under 200 ml of distilled, deionized water, and deaerated for one hour. At the end of the hour, the supernatant is discarded.

7. The procedure of step 6, above, is repeated two more times.

8. The glucose oxidase solution of step 4, above, is then added to the deaerated alumina of step 7, above.

9. To the solution of step 8, above, is added one gram of CMC, i.e. 1-cyclohexyl-3(2-morpholinethyl)-carbodiimide metho-p-toluene sulfonate crystals.

10. The pH of the solution is then adjusted to pH 4.

11. Dissolve into 40 ml distilled deionized water one-and-a-half grams CMC (see step 9, above).

12. The solution prepared in step 11, above, is added at a rate of 1/10 ml per minute, by pump, to the mixture prepared in step 9, above.

13. The reaction of step 12, above, is then allowed to continue for 12 to 16 hours, at 0° C. to 5° C., on the laboratory shaker.

14. The final product is washed with two liters 2/10 molar acetate buffer, pH 5.5.

15. The preparation is then stored under 10 to 15 ml of 1/100 molar phosphate buffer, pH 5.6, and is stored in the refrigerator at 0° C. to 4° C.

16. The activity of this final product is measured:

a. The glucose oxidase activity in a 1/100 molar beta-d-glucose (Sigma Chemical Company) solution, buffered to 1/100 molar acetate, pH 5.5, is measured as 90 units per milliliter of alumina-glucose oxidase composite.

b. The coimmobilized catalase activity in a one percent hydrogen peroxide (Fisher Scientific Company) buffered to 1/100 molar acetate, pH 5.5. is measured as four Units per milliliter of alumina-glucose oxidase composite.

EXAMPLE 11

IMMOBILIZED GLUCOSE OXIDASE

Thirty g of −60+70 mesh, porous alumina having about 0.1 micron diameter pore size is sieved through an 80 mesh screen for five minutes. After the alumina is washed with one liter of distilled, deionized water, it is placed under 200 ml of 6 N HCl for one hour. Sufficient glucose oxidase (Sigma Chemical Co., Type II) is dissolved in 30 ml of distilled water to give an adsorbance of 1.16 at 450 nm and the pH adjusted with 0.1 N HCl or NaOH to pH 7.5. Ten mg of succinic anhydride dissolved in 1 ml of acetone is added to the glucose oxidase solution in 0.1 ml aliquots. One aliquot is added every ten minutes and the solution is stirred for 20 minutes after complete addition. After the alumina is washed of HCl solution and deaerated in the presence of 200 ml of distilled water, the wet alumina is mixed with the succinic anhydride treated, glucose oxidase solution. The pH is adjusted to 4.2 and 0.1 g of 1-ethyl-3-(3-dimethylaminopropyl)-carbodiimide HCl (EDC) is added. This combination of material is allowed to react overnight (16–18 hours) at 0°–5° C. with gentle shaking. During this reaction time, a solution of 0.4 g EDC in 30 ml distilled water is added at the rate of about 0.1 ml/min. The next day, the pH is 5.7 and the adsorbance 0.221 at 450 nm. The alumina-glucose oxidase composite is washed with 2 liters of 0.2 M $(NH_4)_2SO_4$ (enzyme grade Schwartz Mann) followed by 4 liters of distilled, deionized water. The composite is stored in distilled water and the initial activity was 57.7 U/ml of $Al_2O_3$.

EXAMPLE 12

IMMOBILIZED GLUCOSE OXIDASE

This procedure is the same as described in Example 4 above, except that the glucose oxidase has an initial adsorbance of 1.07 and was chromatographed on hexyl hydrophobic gel. The pH of the reaction mixture was 4.1 and the adsorbance at 450 nm was 0.261. The initial activity was 24 U/ml of $Al_2O_3$.

EXAMPLE 13

PREPARATION OF GLUCOSE OXIDASE ON HEXYL HYDROPHOBIC GEL

Eight g of Sigma Chemical Co., Type II glucose oxidase is dissolved in 10 ml of distilled water and dialyzed overnight against 2 mM $PO_4$, pH 7.0. The resulting solution (approximately 50 ml) is applied to a column of n-hexyl hydrophobic gel (Miles Laboratories, Inc.) (1 cm × 30 cm). The column is eluted with 2 mM

21

PO₄ buffer, pH 7 and any protein material eluted is discarded. Next, the column is eluted with 0.05 M PO₄ buffer, pH 7 and the protein eluted contained glucose oxidase which is used for enzyme immobilization.

EXAMPLE 14

A continuous stream determination of the disaccharide glucose-based sugar maltose is accomplished by injecting an aqueous sample of about 2–5 μl of the glucose contaminated maltose into the flowing stream as illustrated in FIG. 1.

The maltose solution containing glucose flows into a scavenger stage composed of coimmobilized glucose oxidase and catalase, and is cleaned of contaminating glucose according to the reactions:

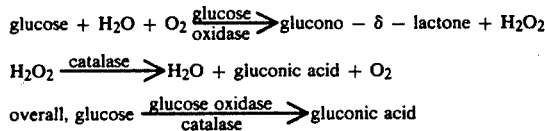

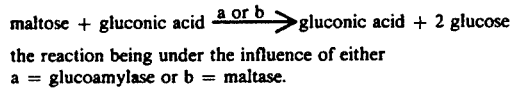

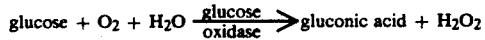

The glucose free maltose sample now flows into a glucose generating stage where the maltose is converted to glucose as follows:

maltose + gluconic acid $\xrightarrow{\text{a or b}}$ gluconic acid + 2 glucose the reaction being under the influence of either
a = glucoamylase or b = maltase.

The resultant glucose flow into a hydrogen peroxide generating stage where the glucose is converted to gluconic acid and hydrogen peroxide as follows:

glucose + O₂ + H₂O $\xrightarrow[\text{oxidase}]{\text{glucose}}$ gluconic acid + H₂O₂

The generated hydrogen peroxide is detected by a flow-through electrochemical sensor, which has a membrane (Spectrapore, MW exclusion limit 12,000–14,000 grams per mole), has been placed between the electrode and the flowing stream.

The signals detected shows a definite linear correlation with the concentration of the injected maltose sample.

For the system described above a flowing buffer system comprising a 1.0 M acetate, pH 5.0–5.6, and 1.0 M in KCl, containing 1–4% Bio-Ban bacteriostat was used, at room temperature.

EXAMPLE 15

A continuous stream determination of the glucose-based trisaccharide maltotriose is accomplished by injecting a 20 μl of a sample of maltotriose contaminated with glucose. The buffer is 0.10 M-sodium acetate, around pH 5.6. The maltotriose solution flows through the apparatus of FIG. 1. The flow rate is about 2 ml per minute. In the scavenger stage coimmobilized glucose oxidase and catalase remove contaminating glucose according to the reactions:

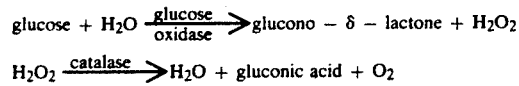

22

-continued

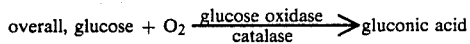

The glucose free maltotriose sample now flows into a glucose generating stage where the maltotriose is converted to glucose as follows:

maltotriose + gluconic acid $\xrightarrow{\text{a or b}}$ gluconic acid + 3 glucose the reaction being under the influence of either
a = glucoamylase or b = maltase.

The resultant glucose flows into a hydrogen peroxide generating stage where the glucose is converted to gluconic acid and hydrogen peroxide as follows:

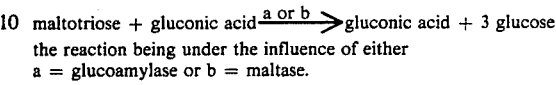

The generated hydrogen peroxide is detected by a flow-through electrochemical sensor, which has a membrane (Spectrapore, MW exclusion limit 12,000–14,000 grams per mole), has been placed between the electrode and the flowing stream.

The signals detected shows a definite linear correlation with the concentration of the injected maltotriose sample.

For the system described above a flowing buffer system comprising a 1.0 M acetate, pH 5.0–5.6, and 1.0 M and KCl, containing 1–5% Bio-Ban bacteriostat was used, at room temperature.

EXAMPLE 16

A sample of starch to be determined is mixed with soluble glucoamylase (about 0.07 mg/ml) was added to a 10 mg % amylose suspension and allowed to react for at least 15 minutes at room temperature. The starch sample is injected just past the scavenger stage and the analysis is carried out just as in Example 14, except that sample is injected just past the scavenger stage. The generated hydrogen peroxide is detected by a flow-through electrochemical sensor, which has a membrane (Spectrapore, MW exclusion limit 12,000–14,000 grams per mole), has been placed between the electrode and the flowing stream.

The signals detected shows a definite linear correlation with the concentration of the injected starch sample.

For the system described above a flowing buffer system comprising a 1.0 M acetate, pH 5.0–5.6, and 1.0 M in KCl, containing 1–5% Bio-Ban bacteriostat was used, at room temperature.

EXAMPLE 17

A sample of starch to be determined is mixed with soluble glucoamylase (about 0.07 mg/ml) was added to a 10 mg % amylose suspension and allowed to react for at least 15 minutes at room temperature. The starch sample is injected just past the scavenger stage and the analysis is carried out just as in Example 14, except that sample is injected just past the scavenger stage.

What is claimed is:

1. An apparatus for the quantitative determination of sugars contained in a fluid sample containing free glucose as a contaminant which comprises, in combination, a reservoir containing a buffer diluent solution and means for flowing said buffer solution as a stream, means for injecting said fluid sample into said flowing stream of buffer solution, first means for passing said flowing stream and including a scavenger enzymatic reagent comprising glucose oxidase and catalase immobilized upon a first solid support for concurrently reacting said free glucose and also hydrogen peroxide resulting from the reaction of said free glucose, the respective quantities of said glucose oxidase and said catalase immobilized on said first solid support being at least sufficient to substantially completely react said free glucose and said resulting hydrogen peroxide, second means for receiving said flowing stream directly from said first means and comprising a glucose generating enzymatic reagent immobilized on a second solid support for reacting with sugars remaining in said flowing stream to produce glucose reaction products, third means for receiving said flowing stream from said second means and comprising a hydrogen peroxide generating enzymatic reagent to react with certain ones of said glucose reaction products to generate hydrogen peroxide, and polarographic detection means for measuring said hydrogen peroxide generated in said flowing stream.

2. The apparatus of claim 1 wherein said glucose generating emzymatic reagent is glucoamylase.

3. The apparatus of claim 1 wherein said glucose generating enzymatic reagent is maltase.

4. The apparatus of claim 1 wherein said first solid support is alumina.

5. The apparatus of claim 1 wherein said second solid support is alumina.

6. The apparatus of claim 1 wherein third solid support is alumina.

* * * * *